United States Patent [19]
Jonczyk et al.

[11] Patent Number: 5,693,612
[45] Date of Patent: Dec. 2, 1997

[54] CYCLOPEPTIDES OF THE FORMULA I

[75] Inventors: Alfred Jonczyk, Darmstadt; Gunter Hölzemann, Seeheim; Simon Goodman, Darmstadt; Horst Kessler, Schwallbach/Ts.; Roland Haubner; Jochen Wermuth, both of Garching, all of Germany

[73] Assignee: Merck Patent Gesellschaft mit Beschrankter Haftung, Darmstadt, Germany

[21] Appl. No.: 430,238

[22] Filed: Apr. 28, 1995

[30] Foreign Application Priority Data

Apr. 30, 1994 [DE] Germany ............. 44 15 310.4

[51] Int. Cl.$^6$ .................................................. A61K 38/00
[52] U.S. Cl. ................. 514/11; 530/317; 930/270
[58] Field of Search ................ 514/11; 530/317; 930/270

[56] References Cited

U.S. PATENT DOCUMENTS

| | | | |
|---|---|---|---|
| 4,472,305 | 9/1984 | Hansen et al. | 260/112.5 R |
| 5,192,746 | 3/1993 | Lobl et al. | 514/11 |
| 5,493,007 | 2/1996 | Burnier et al. | 530/317 |

FOREIGN PATENT DOCUMENTS

| | | |
|---|---|---|
| 2120303 | 10/1994 | Canada . |
| 406 428 | 1/1991 | European Pat. Off. . |
| 0 578 083 | 1/1994 | European Pat. Off. . |
| 43 10 643 | 10/1994 | Germany . |

OTHER PUBLICATIONS

Neubert et al., "Synthese cyclischer under cyclisch–verzweigter . . . ", *Pharmazie* 40 (1985), H. 8, pp. 532–535 no month given.

Smith et al., "Interaction of Integrins $\alpha_v\beta_3$ and Glycoprotein IIB . . . ", *J. Biol. Chem.* 265, 12267–12271, (1990) no month given.

Aumailley et al., FEBS, vol. 291(1):50–54, Oct., 1991.

Kumagai et al., Biochemical & Biophysical Res. Com., vol. 177(1), May 1991, pp. 74–82.

Chemical Abstracts, 119(5):49882d (Aug. 2, 1993).

Chemical Abstracts, 118(17):169613t (Apr. 26, 1993).

*Primary Examiner*—Cecilia J. Tsang
*Assistant Examiner*—C. Delacroix-Muirheid
*Attorney, Agent, or Firm*—Millen, White, Zelano, & Branigan, P.C.

[57] ABSTRACT

The invention relates to novel cyclopeptides of the formula I $$\text{cyclo-(Arg-A-Asp-R}^1\text{-R}^2\text{)} \qquad \text{I}$$

in which
A, $R^1$ and $R^2$ have the meaning given in claim 1, and their salts.

These compounds act as integrin inhibitors and can be used in particular for the prophylaxis and treatment of disorders of the circulation, bones and in tumour therapy, and as antimicrobial and antiviral active compounds.

9 Claims, No Drawings

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:4
        ( D ) OTHER INFORMATION:/product="(S)-Gly[ANC-2]-Leu"
            / note="(S)-Gly-[ANC-2]-Leu =(S)-2-(3-Amino-1-pyrrolid-2-
            onyl)-4- methylpentanoic acid"

( i x ) FEATURE:
        ( A ) NAME/KEY: Modified-site
        ( B ) LOCATION:1
        ( D ) OTHER INFORMATION:/product="Arg(Mtr)"
            / note="Mtr =4-methoxy-2,3,6-trimethylphenylsulfonyl"

( x i ) SEQUENCE DESCRIPTION: SEQ ID NO: 1:

Arg   Gly   Asp   Xaa
    1

( 2 ) INFORMATION FOR SEQ ID NO: 2:

( i ) SEQUENCE CHARACTERISTICS:
- ( A ) LENGTH: 4 amino acids
- ( B ) TYPE: amino acid
- ( C ) STRANDEDNESS: single
- ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
- ( A ) NAME/KEY: Modified-site
- ( B ) LOCATION:1
- ( D ) OTHER INFORMATION:/product="Arg(Mtr)"
  / note="Mtr =4-methoxy-2,3,6-trimethylphenylsulfonyl"

( i x ) FEATURE:
- ( A ) NAME/KEY: Modified-site
- ( B ) LOCATION:4
- ( D ) OTHER INFORMATION:/product="(R)-Gly[ANC-2]-Leu"
  / note="(R)-Gly-[ANC-2]-Leu =(R)-2-(3-Amino-1-pyrrolid-2-
  onyl)-4- methylpentanoic acid"

( x i ) SEQUENCE DESCRIPTION: SEQ ID NO: 2:

Arg  Gly  Asp  Xaa
1

( 2 ) INFORMATION FOR SEQ ID NO: 3:

( i ) SEQUENCE CHARACTERISTICS:
- ( A ) LENGTH: 4 amino acids
- ( B ) TYPE: amino acid
- ( C ) STRANDEDNESS: single
- ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
- ( A ) NAME/KEY: Modified-site
- ( B ) LOCATION:4
- ( D ) OTHER INFORMATION:/product="(S,S)-spiro-Pro-Leu"
  / note="(S,S)-spiro-Pro-Leu =(S,S)-2-(1,7-Diaza-
  spiro[4,4]- oxononan-7-yl)-4-methylpentanoic acid"

( x i ) SEQUENCE DESCRIPTION: SEQ ID NO: 3:

Arg  Gly  Asp  Xaa
1

( 2 ) INFORMATION FOR SEQ ID NO: 4:

( i ) SEQUENCE CHARACTERISTICS:
- ( A ) LENGTH: 5 amino acids
- ( B ) TYPE: amino acid
- ( C ) STRANDEDNESS: single
- ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
- ( A ) NAME/KEY: Modified-site (B) LOCATION: 1
(D) OTHER INFORMATION:/product="Arg(Mtr)"
  / note="Mtr =4-methoxy-2,3,6-trimethylphenylsulfonyl"

(ix) FEATURE:
  (A) NAME/KEY: Modified-site
  (B) LOCATION:4
  (D) OTHER INFORMATION:/product="Btd"
    / note="Btd =8-Amino-4-thiapiperolidin-9-one-2-carboxylic acid"

(xi) SEQUENCE DESCRIPTION: SEQ ID NO: 4:

Arg Gly Asp Xaa Val
1               5

(2) INFORMATION FOR SEQ ID NO: 5:

(i) SEQUENCE CHARACTERISTICS:
    (A) LENGTH: 4 amino acids
    (B) TYPE: amino acid
    (C) STRANDEDNESS: single
    (D) TOPOLOGY: circular (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:4
    (D) OTHER INFORMATION:/product="(S)-Gly[ANC-2]-Leu"
      / note="(S)-Gly-[ANC-2]-Leu =(S)-2-(3-Amino-1-pyrrolid-2-onyl)-4- methylpentanoic acid"

(xi) SEQUENCE DESCRIPTION: SEQ ID NO: 5:

Arg Gly Asp Xaa
1

(2) INFORMATION FOR SEQ ID NO: 6:

(i) SEQUENCE CHARACTERISTICS:
    (A) LENGTH: 4 amino acids
    (B) TYPE: amino acid
    (C) STRANDEDNESS: single
    (D) TOPOLOGY: circular (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:4
    (D) OTHER INFORMATION:/product="(R)-Gly[ANC-2]-Leu"
      / note="(R)-Gly-[ANC-2]-Leu =(R)-2-(3-Amino-1-pyrrolid-2-onyl)-4- methylpentanoic acid"

(xi) SEQUENCE DESCRIPTION: SEQ ID NO: 6:

Arg Gly Asp Xaa
1

(2) INFORMATION FOR SEQ ID NO: 7:

(i) SEQUENCE CHARACTERISTICS:
    (A) LENGTH: 4 amino acids
    (B) TYPE: amino acid ( C ) STRANDEDNESS: single
          ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
          ( A ) NAME/KEY: Modified-site
          ( B ) LOCATION:1
          ( D ) OTHER INFORMATION:/product="Arg(Mtr)"
                / note="Mtr =4-methoxy-2,3,6-trimethylphenylsulfonyl"

( i x ) FEATURE:
          ( A ) NAME/KEY: Modified-site
          ( B ) LOCATION:4
          ( D ) OTHER INFORMATION:/product="(S,S)-spiro-Pro-Leu"
                / note="(S,S)-spiro-Pro-Leu =(S,S)-2-(1,7-Diaza-
                spiro[4,4]- oxononan-7-yl)-4-methylpentanoic acid"

( x i ) SEQUENCE DESCRIPTION: SEQ ID NO: 7:

Arg  Gly  Asp  Xaa
     1

( 2 ) INFORMATION FOR SEQ ID NO: 8:

( i ) SEQUENCE CHARACTERISTICS:
          ( A ) LENGTH: 5 amino acids
          ( B ) TYPE: amino acid
          ( C ) STRANDEDNESS: single
          ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
          ( A ) NAME/KEY: Modified-site
          ( B ) LOCATION:4
          ( D ) OTHER INFORMATION:/product="Btd"
                / note="Btd =3-Amino-4-thiapiperolidin-9-one-2-carboxylic
                acid"

( x i ) SEQUENCE DESCRIPTION: SEQ ID NO: 8:

Arg  Gly  Asp  Xaa  Val
     1                   5

( 2 ) INFORMATION FOR SEQ ID NO: 9:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
          ( A ) NAME/KEY: Modified-site
          ( B ) LOCATION:1
          ( D ) OTHER INFORMATION:/product="Arg(Mtr)"
                / note="Mtr =4-methoxy-2,3,6-trimethylphenylsulfonyl"

( i x ) FEATURE:
    ( A ) NAME/KEY: Modified-site
    ( B ) LOCATION:3
    ( D ) OTHER INFORMATION:/product="Asp(ONa)"

( i x ) FEATURE:
    ( A ) NAME/KEY: Modified-site
    ( B ) LOCATION:4
    ( D ) OTHER INFORMATION:/product="Btd"
        / note="Btd =8-Amino-4-thiapiperolidin-9-one-2-carboxylic acid"

( x i ) SEQUENCE DESCRIPTION: SEQ ID NO: 9:

Arg Gly Asp Xaa
1

( 2 ) INFORMATION FOR SEQ ID NO: 10:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:3
    ( D ) OTHER INFORMATION:/product="Asp(O(CH2)3-CONH-(CH2)3-polymer)"

( i x ) FEATURE:
    ( A ) NAME/KEY: Modified-site
    ( B ) LOCATION:4
    ( D ) OTHER INFORMATION:/product="Btd"
        / note="Btd =8-Amino-4-thiapiperolidin-9-one-2-carboxylic acid"

( x i ) SEQUENCE DESCRIPTION: SEQ ID NO: 10:

Arg Gly Asp Xaa
1

( 2 ) INFORMATION FOR SEQ ID NO: 11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:3
    ( D ) OTHER INFORMATION:/product="Asp(O(CH2)3-CONH-(CH2)3-polymer)"

( i x ) FEATURE:
    ( A ) NAME/KEY: Modified-site
    ( B ) LOCATION:4
    ( D ) OTHER INFORMATION:/product="Btd"

/ note="Btd =8-Amino-4-thiapiperolidin-9-one-2-carboxylic
acid"

( x i ) SEQUENCE DESCRIPTION: SEQ ID NO: 11:

Arg Gly Asp Xaa
1

( 2 ) INFORMATION FOR SEQ ID NO: 12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:3
        ( D ) OTHER INFORMATION:/product="Asp(NH-(CH2)3-0-polymer)"

( i x ) FEATURE:
        ( A ) NAME/KEY: Modified-site
        ( B ) LOCATION:4
        ( D ) OTHER INFORMATION:/product="Btd"
            / note="Btd =8-Amino-4-thiapiperolidin-9-one-2-carboxylic
            acid"

( x i ) SEQUENCE DESCRIPTION: SEQ ID NO: 12:

Arg Gly Asp Xaa Val
1                    5

( 2 ) INFORMATION FOR SEQ ID NO: 13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:4
        ( D ) OTHER INFORMATION:/product="Btd"
            / note="Btd =8-Amino-4-thiapiperolidin-9-one-2-carboxylic
            acid"

( x i ) SEQUENCE DESCRIPTION: SEQ ID NO: 13:

Arg Gly Asp Xaa
1

( 2 ) INFORMATION FOR SEQ ID NO: 14:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: circular

```
        ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:1
                ( D ) OTHER INFORMATION:/product="Arg(Mtr)"
                        / note="Mtr =4-methoxy-2,3,6-trimethylphenylsulfonyl"

( i x ) FEATURE:
                ( A ) NAME/KEY: Modified-site
                ( B ) LOCATION:4
                ( D ) OTHER INFORMATION:/product="Btd"
                        / note="Btd =8-Amino-4-thiapiperolidin-9-one-2-carboxylic
                            acid"

( x i ) SEQUENCE DESCRIPTION: SEQ ID NO: 14:

Arg  Gly  Asp  Xaa
            1

( 2 ) INFORMATION FOR SEQ ID NO: 15:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: circular ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO: 15:

Gln  Phe  Phe  Gly  Leu  Met
            1                   5
```

CYCLOPEPTIDES OF THE FORMULA I

BACKGROUND OF THE INVENTION

The invention relates to novel cyclopeptides of the formula I cyclo-(Arg-A-Asp-R$^1$-R$^2$)    I in which A is Gly or Ala, R$^1$ is a 2-carboxy-8-amino-4-thiapiperolidin-9-one (Btd), o-aminomethylo'-carboxybiphenyl (Biph), 2-aminomethyl-5-carboxymethyl-thiophene (Act) or 6-aminohexanoic acid radical (Aha) or a 2-(1,7-diazaspiro-[4,4]nonan-7-yl)-4-methylpentanoic acid ((S,S)spiro-Pro-Leu) or 2-(3-amino-1-pyrrolid-2-onyl)-4-methylpentanoic acid radical ((S) Gly[ANC-2]-Leu or (R) Gly[ANC-2]-Leu), the radicals in each case being bonded via peptide bonds, and R$^2$ is absent, or else is Val, and also their physiologically acceptable salts.

In Pharmazie 40 (8), 532–5 (1985), a cyclohexapeptide is disclosed, having a sequence of cyclo-(Gln-Phe-Phe-Gly-Leu-Met) (SEQ ID NO: 15). It showed only a small kinin activity on isolated guinea pig ileum compared to substance P, but it is a full agonist.

SUMMARY OF THE INVENTION

An object of the invention was to find novel compounds having useful properties, in particular those which can be used for the production of medicaments.

Upon further study of the specification and appended claims, further objects and advantages of this invention will become apparent to those skilled in the art.

It has been found that the compounds of the formula I and their salts have very useful properties. In particular, they act as integrin inhibitors, in which case they particularly inhibit the interactions of $\beta_3$- or $\beta_5$-integrin receptors with ligands. The compounds are particularly effective in the case of the integrins $\alpha_v\beta_1$, $\alpha_v\beta_3$, $\alpha_v\beta_5$, $\alpha_v\beta_6$ and $\alpha_{IIb}\beta_3$. This action can be demonstrated, for example, by the method which is described by J. W. Smith et al. in J. Biol. Chem. 265, 12267–12271 (1990). In addition, there are anti-inflammatory effects. All these actions can be demonstrated with the aid of methods which are known from the literature.

The compounds can be employed as pharmaceutical active compounds in human and veterinary medicine, in particular for the prophylaxis and the treatment of disorders of the circulation, thrombosis, cardiac infarct, arteriosclerosis, inflammations, apoplexy, angina pectoris, tumor disorders, osteolytic disorders, in particular osteoporosis, for angiogenesis and restenosis after angioplasty. The compounds may furthermore be employed to improve the healing of wounds. Compounds according to formula I of the present invention can also be used as commercial research tools, e.g., to purify integrins, such as by affinity chromatography, or to determine the binding affinity of various ligands to integrin or other receptors.

The compounds are additionally suitable as antimicrobial and antiviral active compounds which prevent infections, such as can be triggered, for example, by bacteria, fungi, yeasts or viruses. The substances can therefore preferably be given as concomitant antimicrobial active compounds when interventions are carried out on organisms and in which exogenous substances, such as e.g. biomaterials, implants, catheters or cardiac pacemakers or the like, are employed. They therefore also act as antiseptics.

The abbreviations of amino acid radicals shown above and below stand for the radicals of the following amino acids:

| | |
|---|---|
| Act | 2-aminomethylthiophene-5-acetic acid |
| Aha | 6-aminohexanoic acid |
| Ala | alanine |
| Asn | asparagine |
| Asp | aspartic acid |
| Asp(OR) | aspartic acid ($\beta$-ester) |
| Arg | arginine |
| Biph | o-aminoethylbiphenyl-o'-carboxylic acid |
| Btd | 8-amino-4-thiapiperolidin-9-one-2-carboxylic acid |
| Cys | cysteine |
| Gln | glutamine |
| Glu | glutamic acid |
| Gly | glycine |
| Gly[ANC-2]—Leu | 2-(3-amino-1-pyrrolid-2-onyl)-4-methylpentanoic acid |
| His | histidine |
| Ile | isoleucine |
| Leu | leucine |
| Lys | lysine |
| Met | methionine |
| Nle | norleucine |
| Orn | ornithine |
| Phe | phenylalanine |
| Pro | proline |
| spiro—Pro—Leu | 2-(1,7-diazaspiro[4,4]-6-oxononan-7-yl)-4-methylpentanoic acid |
| Ser | serine |
| Thr | threonine |
| Trp | tryptophan |
| Tyr | tyrosine |
| Val | valine. |

In addition, the following have the meanings below:

| | |
|---|---|
| BOC | tert-butoxycarbonyl |
| CBZ | benzyloxycarbonyl |
| DCCI | dicyclohexylcarbodiimide |
| DMF | dimethylformamide |
| EDCI | N-ethyl-N'-(3-dimethylaminopropyl)-carbodiimide hydrochloride |
| Et | ethyl |
| FMOC | 9-fluorenylmethoxycarbonyl |
| HOBt | 1-hydroxybenzotriazole |
| Me | methyl |
| Mtr | 4-methoxy-2,3,6-trimethylphenyl-sulfonyl |
| OBut | tert-butoxy |
| OMe | methoxy |
| OEt | ethoxy |
| POA | phenoxyacetyl |
| TBTU | 2-(1H-benzotriazol-1-yl)-1,1,3,3-tetra-methyluronium tetrafluoroborate |
| TFA | trifluoroacetic acid. |

If the amino acids mentioned above can occur in several enantiomeric forms, then all these forms and also their mixtures (e.g. the DL-forms) are included above and below, e.g. as constituents of the compounds of the formula I. When a compound according to formula I comprises a mixture of D- and L-isomers, the isomers can be separated according to conventional methods as known in the art. The amino acids, e.g. as constituents of compounds of the formula I, may furthermore be provided with appropriate protective groups known per se.

The invention further relates to a process for the preparation of a compound of the formula I or one of its salts, characterized in that it is liberated from one of its functional derivatives by treating with a solvolysing or hydrogenolysing agent, or in that a peptide of the formula II

H—Z—OH    II in which
Z is -Arg-A-Asp-R¹-R²-
-A-Asp-R¹-R²-Arg-
-Asp-R¹-R²-Arg-A-
-R¹-R²-Arg-A-Asp- or
-R²-Arg-A-Asp-R¹-, or a reactive derivative of such a peptide is treated with a cyclizing agent, and/or in that a basic or acidic compound of the formula I is converted into one of its salts by treating with an acid or base.

The radicals A, R¹, R² and Z above and below have the meanings given in the formulae I and II, if not expressly stated otherwise.

The radical (S,S)spiro-Pro-Leu is a 2-(1,7-diazaspiro[4,4]-6-oxononan-7--yl)--4-methylpentanoic acid radical and has the following structure:

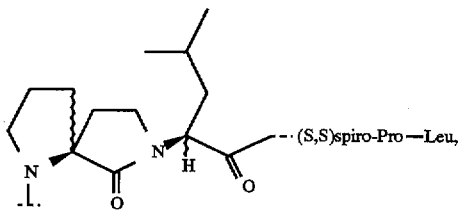

while the radical (S)Gly[ANC-2]-Leu or (R)Gly[ANC-2]-Leu is a 3(S)- or 3(R)-2-(3-amino-1-pyrrolid-2-onyl)-4-methylpentanoic acid radical

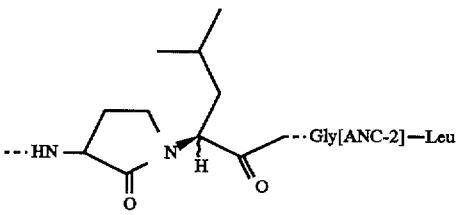

Biph is an o-aminomethylbiphenyl-o'-carboxylic acid radical, Biph 1 and Biph 2 being possible atropisomers.

For the radical R¹ just as for the radical R², all previously given definitions are equally preferred. The invention thus equally relates to cyclic penta- and tetrapeptides.

A is preferably Gly, but can also be Ala, in particular DAla, i.e., D-Ala, a D-isomer.

The compounds of the formula I and also the starting materials for their preparation are otherwise prepared by known methods, as are described in the literature (e.g. in the standard works such as Houben-Weyl, Methoden der organischen Chemie, (Methods of Organic Chemistry) Georg-Thieme-Verlag, Stuttgart), in particular under reaction conditions which are known and suitable for the said reactions. In this context, use can also be made of known variants which are not mentioned in more detail here.

The peptide component Gly[ANC-2]-Leu in the (R)- and (S)-form can be prepared by the method of R. M. Freidinger et al., described in J. Org. Chem. 47, 104 (1982). The component spiro-Pro--Leu can be prepared, for example, in analogy to the method of P. Ward et al., J. Med. Chem. 33, 1848 ff. (1990), while a synthesis of Btd is possible according to U. Nagai et al., Tetrahedron 4.9, 3577–3592 (1993).

The starting substances can also be formed in situ, if desired, such that they are not isolated from the reaction mixture, but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry an amino protecting group instead of an H atom which is bonded to an N atom, e.g. those which correspond to the formula I, but contain an NHR' group (in which R' is an amino protecting group, e.g. BOC or CBZ) instead of an $NH_2$ group.

In addition, starting materials are preferred which carry a hydroxyl protecting group instead of the H atom of a hydroxyl group, e.g. those which correspond to the formula I, but contain an R"O-phenyl group (in which R" is a hydroxyl protecting group) instead of a hydroxyphenyl group.

Several—identical or different—protected amino and/or hydroxyl groups can be present in the molecule of the starting material. If the protective groups present are different from one another, in many cases they can be removed selectively.

The expression "amino protecting group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. As the amino protecting groups are removed after the desired reaction (or reaction sequence), their nature and size is otherwise not critical; but those having 1–20, in particular 1–8, C atoms are preferred. The expression "acyl group" is to be taken in its widest sense in connection with the present process. It includes acyl groups derived from aliphatic, araliphatic, aromatic or heterocyclic carboxylic acids or sulfonic acids and in particular alkoxycarbonyl, aryloxycarbonyl and, above all, aralkoxycarbonyl groups. Examples of acyl groups of this type are alkanoyl such as acetyl, propionyl or butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxy-carbonyl; aralkyloxycarbonyl such as CBZ ("carbo-benzoxy"), 4-methoxybenzyloxycarbonyl, FMOC, and arylsulfonyl such as Mtr. Preferred amino protecting groups are BOC and Mtr, and in addition CBZ, FMOC, benzyl and acetyl.

The expression "hydroxyl protecting group" is also generally known and relates to groups which are suitable for protecting a hydroxyl group from chemical reactions, but which are easily removable, after the desired chemical reaction has been carried out at other positions in the molecule. Typical groups of this type are the abovementioned unsubstituted or substituted aryl, aralkyl or acyl groups, and in addition also alkyl groups. The nature and size of the hydroxyl protecting groups is not critical, as they are removed after the desired chemical reaction or reaction sequence; preferred groups are those having 1–20, in particular 1–10 C atoms. Examples of hydroxyl protecting groups are, inter alia, benzyl, p-nitrobenzoyl, p-toluenesulfonyl, tert-butyl and acetyl; benzyl and tert-butyl being particularly preferred. The COOH groups in aspartic acid and glutamic acid are preferably protected in the form of their tert-butyl esters (e.g. Asp (OBut)).

The functional derivatives of the compounds of the formula I to be used as starting materials can be prepared by customary methods of amino acid and peptide synthesis, such as are described e.g. in the standard works and patent applications mentioned, and e.g. also by the Merrifield solid phase method (B. F. Gysin and R. B. Merrifield, J. Am. Chem. Soc. 94, 3102 et seq. (1972)). Synthesis according to FMOC strategy in a flow reactor, described by A. Jonczyk and J. Meienhofer in Peptides, Proc. 8th Am. Pept. Symp. 73–77 (1983) (Eds. V. J. Hruby and D. H. Rich), Pierce Co. Rockford, is particularly advantageous.

The liberation of the compounds of the formula I from their functional derivatives is carried out—depending on the protecting group used—e.g. with strong acids, preferably with TFA or perchloric acid, but also with other strong inorganic acids such as hydrochloric acid or sulfuric acid, or strong organic carboxylic acids such as trichloroacetic acid or sulfonic acids such as benzene- or p-toluenesulfonic acid. The presence of an additional inert solvent is possible, but not always necessary. Suitable inert solvents are preferably organic, for example carboxylic acids such as acetic acid, ethers such as tetrahydrofuran or dioxane, amides such as DMF, halogenated hydrocarbons such as dichloromethane, and in addition also alcohols such as methanol, ethanol or isopropanol and also water.

In addition, mixtures of the abovementioned solvents are suitable. TFA is preferably used in an excess without addition of a further solvent, perchloric acid in the form of a mixture of acetic acid and 70% perchloric acid in the ratio 9:1. The reaction temperatures for the cleavage are preferably about 0°–50°, more preferably about 15°–30° (room temperature).

The groups BOC, OBut and Mtr can be removed e.g. preferably using TFA in dichloromethane or with about 3 to 5N HCl in dioxane at about 15°–30°, the FMOC group using an about 5–50% solution of secondary amines, such as dimethylamine, diethylamine or piperidine, in DMF at about 15°–30°.

Protecting groups which can be removed by hydrogenolysis (e.g. CBZ or benzyl) can be removed, e.g. by treating with hydrogen in the presence of a catalyst (e.g. a noble metal catalyst such as palladium, preferably on a carrier such as carbon). Suitable solvents in this case are those mentioned above, in particular e.g. alcohols such as methanol or ethanol or amides such as DMF. The hydrogenolysis is carried out, typically, at temperatures about 0°–100° and pressures about 1–200 bar, preferably at 20°–30° and 1–10 bar. Hydrogenolysis of the CBZ group is easily carried out e.g. on about 5–10% Pd-C in methanol or using ammonium formate (instead of H2) on Pd-C in methanol/DMF at about 20°–30°.

Compounds of the formula I can also be obtained by cyclization of compounds of the formula II under the conditions of a peptide synthesis. In this case, the reaction is preferably carried out by customary methods of peptide synthesis, as are described e.g. in Houben-Weyl, loc cit. volume 15/II, pages 1 to 806 (1974).

The cyclization reaction is preferably carried out in the presence of a cyclizing agent such as a dehydrating agent, e.g. a carbodiimide such as DCCI or EDCI, and in addition propanephosphonic anhydride (compare Angew. Chem. 92, 129 (1980)), diphenylphosphoryl azide or 2-ethoxy-N-ethoxy-carbonyl-1,2-dihydroquinoline, in an inert solvent, e.g. a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures between about −10°–40°, preferably about 0°–30°. In order to promote intramolecular cyclization before intermolecular peptide bonding, it is preferable to work in dilute solutions (dilution principle).

Instead of II, suitable reactive derivatives of these substances can also be employed in the reaction, e.g. those in which reactive groups are intermediately blocked by protecting groups. The amino acid derivatives II can be used e.g. in the form of their activated esters which are preferably formed in situ, e.g. by addition of HOBt or N-hydroxysuccinimide.

The starting materials of the formula II are, as a rule, novel. They can be prepared by known methods, e.g. the abovementioned methods of peptide synthesis and of removal of protective groups.

As a rule, protected pentapeptide esters of the formula R'-Z-OR", e.g. BOC-Z-OMe or BOC-Z-OEt, are initially synthesized, which are first hydrolysed to give acids of the formula R'-Z-OH, e.g. BOC-Z-OH; the protective group R' is removed from these, by means of which the free peptides of the formula H-Z-OH (II) are obtained.

A base of the formula I can be converted into the appropriate acid addition salt using an acid. Suitable acids for this reaction are in particular those which yield physiologically acceptable salts. Inorganic acids can thus be used, e.g. sulfuric acid, nitric acid, hydrohalic acids such as hydrochloric acid or hydrobromic acid, phosphoric acids such as orthophosphoric acid and sulfamic acid, and in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and-disulfonic acids, and laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Suitable salts here are in particular the sodium, potassium, magnesium, calcium and ammonium salts, and also substituted ammonium salts, e.g. the dimethyl-, diethyl- or diisopropylammonium salts, monoethanol-, diethanol- or triethanolammonium salts, cyclohexyl- or dicyclohexyl-ammonium salts, dibenzylethylene-diammonium salts, and furthermore e.g. salts with N-methyl-D-glucamine or with arginine or lysine.

The novel compounds of the formula I and their physiologically acceptable salts can be used for the production of pharmaceutical preparations by bringing them into a suitable dosage form together with at least one excipient or auxiliary and, if desired, together with one or more other active compound(s). The preparations thus obtained can be employed as medicaments in human or veterinary medicine. Suitable excipient substances are organic or inorganic substances which are suitable for enteral (e.g. oral or rectal), parenteral (e.g. intravenous injection) or local (e.g. topical, dermal, ophthalmic or nasal) administration or for administration in the form of an inhalant spray and which do not react with the novel compounds, for example water or aqueous isotonic saline solution, lower alcohols, vegetable oils, benzyl alcohols, polyethylene glycols, glycerol triacetate and other fatty acid glycerides, gelatin, soya lecithin, carbohydrates such as lactose or starch, magnesium stearate, talc, cellulose and petroleum jelly. Tablets, coated tablets, capsules, syrups, juices or drops, in particular, are used for oral administration; film tablets and capsules having enteric coatings or capsule shells are especially of interest. Suppositories are used for rectal administration, and solutions, preferably oily or aqueous solutions, and in addition suspensions, emulsions or implants, are used for parenteral administration. Solutions, e.g., which can be used in the form of eye drops, and in addition, e.g. suspensions, emulsions, creams, ointments or compresses are suitable for topical application. Sprays can be used which contain the active compound either dissolved or suspended in a propellant gas or propellant gas mixture (e.g. $CO_2$ or chlorofluorohydrocarbons) for administration as inhalant sprays. The active compound here is preferably used in micronized form, it being possible for one or more additional physiologically tolerable solvents to be present, e.g. ethanol. Inhalant solutions can be administered with the aid of customary inhalers. The novel compounds can also be lyophilized and the lyophilizates obtained used e.g. for the production of injection preparations. The injections can be administered as a bolus or as a continuous infusion (e.g. intravenous, intramuscular, subcutaneous or intrathecal). The preparations indicated can be sterilized and/or can contain auxiliaries such as preservatives, stabilizers and/or wetting agents, emulsifiers, salts for influencing osmotic pressure, buffer substances, colorants and/or flavourings. If desired, they can also contain one or more other active compounds, e.g. one or more vitamins.

The substances according to the invention can be administered in analogy to other known commercially available peptides, but in particular in analogy to the compounds described in U.S. Pat. No. A-4,472,305, preferably in dosages about 0.05–500 mg, in particular about 0.5–100 mg per dosage unit. The daily dose is preferably about 0.01–2 mg/kg of body weight. The latter dosages are suitable for, e.g., parenteral administration. The specific dose for each intended patient depends, however, on many different factors, for example the activity of the specific compound employed, the age, body weight, general state of health, sex, the diet, the time and route of administration, and the rate of excretion, pharmaceutical combination and severity of the particular disorder to which the therapy applies. Parenteral administration is preferred.

In addition, the novel compounds of the formula I can be used, e.g., as integrin ligands for the preparation of columns for affinity chromatography for the preparation of integrins in pure form. A cyclopeptide according to formula I can be bound a solid support matrix to form an affinity chromatography material which can be used to purify or separate (e.g., from a tissue or cell homogenate or other mixture) integrin from other components. Such a method of use can involve, e.g., contacting the material with a sample containing integrin under conditions in which the integrin binds to the ligand (i.e., effective conditions), eluting the integrin from the column, and collecting enriched or purified integrin. The integrin can be finally eluted from the cyclopeptide ligand by, e.g., the treatment with a surplus of ethylenediamine-N, N,N',N',-tetraacetate (EDTA)-solution or another complexing agent or by the treatment with a surplus of a peptide solution, itself. The peptide molecules displace the integrins so that the free integrin is eluted and isolated by usual working-up methods.

The ligand, i.e. a peptide derivative of the formula I, is in this case covalently coupled to a polymeric support via anchor functions.

Suitable polymeric support materials are the polymeric solid phases known per se in peptide chemistry, having preferably hydrophilic properties, for example crosslinked polysugars, such as cellulose, Sepharose or Sephadex, acrylamides, polymers based on polyethylene glycol or Tentakel polymers®.

Suitable anchor functions which are linked to the polymeric supports are preferably linear alkylene chains having 2–12 C atoms, which are bonded directly to the polymer at one end and have a functional group, such as e.g. hydroxyl, amino, mercapto, maleimido or —COOH, at the other end and are suitable to be linked to a functional side chain of the respective peptide.

It is possible in this case that the peptide be bonded directly or likewise via a second anchor function to the anchor of the polymer.

Moreover, certain amino acid radicals which are a constituent of the peptides of the formula I can be modified in their side chains in such a way that they are available for anchorage via e.g. SH, OH, $NH_2$ or COOH groups with the anchor of the polymer.

Examples of amino acid radicals whose side chain can be used directly as an anchor function are e.g. Arg or Asp.

Examples of anchors which can be bonded via free $NH_2$ groups are radicals such as e.g. —CO—$C_nH_{2n}$—$NH_2$, —CO—$C_nH_{2n}$—OH, —CO—$C_nH_{2n}$—SH or —CO—$C_nH_{2n}$—COOH where n=2–12, where the length of the alkylene chain is not critical and this can optionally also be replaced e.g. by appropriate aryl or alkylaryl radicals.

C-terminal anchors which can be linked to free acid groups are, for example, —O—$C_nH_{2n}$—SH, —O—$C_nH_{2n}$—OH, —O—$C_nH_{2n}$—$NH_2$, —O—$C_nH_{2n}$—COOH, —NH—$C_nH_{2n}$—SH, —NH—$C_nH_{2n}$—OH, —NH—$C_nH_{2n}$— or —NH—$C_nH_{2n}$—COOH, where for n and the alkylene chain what has already been said in the preceding section applies.

The preparation of the materials for affinity chromatography for purifying integrins is carried out under conditions such as are customary for the condensation of amino acids and are known per se and have already been outlined in the section for the preparation of the compounds of the formula I.

In the case of the thiol-containing anchors, addition reactions, such as Michael addition to maleimide derivatives or disulphide formation with a polymer-bonded thiol, are available.

All temperatures above and below are stated in °C. In the following examples, "customary working up" means: water is added, if necessary, the mixture is neutralized and extracted with ether or dichloromethane, the organic phase is separated off, dried over sodium sulfate, filtered and evaporated and the residue is purified by chromatography on silica gel and/or crystallization. RT=retention time (minutes) for HPLC on System A: Lichrosorb® RP select B (250×4; 5 μm) or System B: Lichrosorb® RP 18 (250×4; 5 μm); eluent (System A): 0.3% TFA in water; isopropanol gradient of 0–80 vol %; 50 min at 1 ml/min. flow and detection at 215 nm. Eluent (System B): eluent A: 0.1% TFA in water; eluent B: 0.1% TFA in acetonitrile/water (9:1); gradient 20–90% B; 50 min at 1 ml/min. M+=molecular peak in the mass spectrum, obtained by the fast atom bombardment method (FAB), the molecular weight indicated being increased by one mass unit in comparison with the calculated value.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celcius and unless otherwise indicated, all parts and percentages are by weight.

There entire disclosures of all applications, patents and publications, cited above and below, and of corresponding German application P 4415310.4, are hereby incorporated by reference.

EXAMPLES

Example 1

A solution of 0.4 g of H-Arg(Mtr)-Gly-Asp-Btd-ONa [e.g. obtainable from FMOC-Arg (Mtr) -Gly-Asp-Btd-O-Wang, -O- Wang being the radical of a 4-oxymethylphenoxymethyl polystyrene resin used in the modified Merrifield techniques, by removal of the FMOC group with piperidine/DMF and removal of the resin with TFA/$CH_2Cl_2$ (1:1)] in 15 ml of DMF is diluted with 85 ml of dichloromethane and treated with 50 mg of $NaHCO_3$. After cooling in a dry ice/acetone mixture, 40 μl of diphenylphosphoryl azide are added. After standing at room temperature for 16 hours, the solution is concentrated. The concentrate is filtered (Sephadex G10 column in isopropanol/water 8:2) and then purified in the customary manner by means of HPLC. Cyclo-(Arg(Mtr)-Gly-Asp-Btd) is obtained.

The following are obtained analogously by cyclization of the corresponding linear peptides:
cyclo (Arg(Mtr)-Gly-Asp-(S)Gly[ANC-2]-Leu) (SEQ ID NO:1);
cyclo-(Arg(Mtr)-Gly-Asp-(R)Gly[ANC-2]-Leu)(SEQ ID NO:2);
cyclo-(Arg(Mtr)-Gly-Asp-(S,S)spiro-Pro-Leu)(SEQ ID NO:7);
cyclo-(Arg(Mtr)-Gly-Asp-Biph1);
cyclo-(Arg(Mtr)-Gly-Asp-Biph2);
cyclo-(Arg(Mtr)-Gly-Asp-Act);
cyclo-(Arg(Mtr)-Gly-Asp-Btd-Val)(SEQ ID NO:4);
cyclo-(Arg(Mtr)-DAla-Asp-Btd-Val);
cyclo-(Arg(Mtr)-Gly-Asp-Aha);
cyclo-(Arg(Mtr)-DAla-AspBtd);
cyclo-(Arg(Mtr)-DAla-Asp-(S)Gly[ANC-2]-Leu);
cyclo-(Arg(Mtr)-DAla-Asp-(R)Gly[ANC-2]-Leu);
cyclo-(Arg(Mtr)-DAla-Asp-(S,S)spiro-Pro-Leu);
cyclo-(Arg(Mtr)-DAla-Asp-Biph1);
cyclo-(Arg(Mtr)-DAla-Asp-Biph2);
cyclo-(Arg(Mtr)-DAla-Asp-Act).

Example 2

A solution of 0.28 g of cyclo-(Arg(Mtr)-Gly-Asp-Btd) (SEQ ID NO:14); [obtainable by cyclization according to Ex. 1] in 8.4 ml of TFA, 1.7 ml of dichloromethane and 0.9 ml of thiophenol is allowed to stand at room temperature for 4 hours, then concentrated and, after diluting with water, freeze-dried. Gel filtration on Sephadex G 10 (acetic acid/water 1:1) and subsequent purification by preparative HPLC under the conditions indicated give cyclo-(Arg-Gly-Asp-Btd)(SEQ ID NO:13); RT=13.2; $M^+527$.

The following are obtained analogously:
from cyclo-(Arg(Mtr)-Gly-Asp-(S)Gly[ANC-2]-Leu)(SEQ ID NO:1): cyclo-(Arg-Gly-Asp-(S)Gly[ANC-2]-Leu) (SEQ ID NO:5); RT=4.8; $M^+525$;
from cyclo-(Arg(Mtr)-Gly-Asp-(R)Gly[ANC-2]-Leu)(SEQ ID NO:2): cyclo-(Arg-Gly-Asp-(R)Gly[ANC-2]-Leu) (SEQ ID NO:6); RT=6.3; $M^+525$;
from cyclo-(Arg(Mtr)-Gly-Asp-(S,S)spiro-Pro-Leu)(SEQ ID NO:3); RT=14.6: $M^+565$; cyclo-(Arg-Gly-Asp-(S,S)spiro-Pro-Leu)(SEQ ID NO:3); RT=14.6; $M^+565$;
from cyclo-(Arg(Mtr)-Gly-Asp-Biph1): cyclo-(Arg-Gly-Asp-Biph1); RT=20.7; $M^+538$;
from cyclo-(Arg(Mtr)Gly-Asp-Biph2): cyclo-(Arg-Gly-Asp-Biph2); RT=20.8; $M^+538$;
from cyclo-(Arg(Mtr)-Gly-Asp-Act): cyclo-(Arg-Gly-Asp-Act), RT=14.3; $M^+547$;
from cyclo(Arg(Mtr)-Gly-Asp-Btd-Val) (SEQ ID NO:4); and cyclo-(Arg-Gly-Asp-Btd-Val)(SEQ ID NO:8);
from cyclo-(Arg(Mtr)-DAla-Asp-Btd-Val): cyclo-(Arg-DAla-Asp-Btd-Val);
from cyclo-(Arg (Mtr)-Gly-Asp-Aha): cyclo-(Arg-Gly-Asp-Aha).

Example 3

80 mg of cyclo-(Arg-Gly-Asp-Btd) (SEQ ID NO:13) are dissolved in 0.01M HCl (SEQ ID NO:13) five to six times and freeze-dried after each dissolving operation. Subsequent purification by HPLC gives cyclo-(Arg-Gly-Asp-Btd)×HCl.

The following are obtained analogously from cyclo-(Arg-Gly-Asp-Aha): cyclo-(Arg-Gly-Asp-Aha)×HCl;
from cyclo-(Arg-Gly-Asp-Btd-Val)(SEQ ID NO:8): cyclo-(Arg-Gly-Asp-Btd-Val)×HCl(SEQ ID NO:8);
from cyclo-(Arg-Gly-Asp-Btd-Val)(SEQ ID NO:8); cyclo-(Arg-DAla-Asp-Btd-Val)×HCl;
from cyclo-(Arg-DAla-Asp-Btd-Val) by treatment with acetic acid: cyclo-(Arg-DAla-Asp-Btd-Val)×$H_3C$—COOH;
from cyclo-(Arg-Gly-Asp-Aha) by treatment with 0.01N nitric acid: cyclo-(Arg-Gly-Asp-Aha)×$HNO_3$.

Example 4

To prepare affinity phases, 0.9 g of Cl—$(CH_2)_3$—CO—NH—$(CH_2)_3$ polymer [obtainable by condensation of Cl—$(CH_2)_3$—COOH with $H_2N$—$(CH_2)_3$ polymer] is suspended in 10 ml of 0.1M sodium phosphate buffer at pH 7 and one equivalent of cyclo-(Arg(Mtr)-Gly-Asp(ONa)-Btd (SEQ ID NO:9) is added at 4°. The reaction mixture is stirred for 4 hours with simultaneous warming to room temperature, and the solid residue is filtered off and washed twice with 10 ml of buffer solution (pH 7) each time and subsequently three times with 10 ml of water each time. Cyclo-(Arg(Mtr)-Gly-Asp(O$(CH_2)_3$—CONH—$(CH_2)_3$— polymer)-Btd) (SEQ ID NO:10) is obtained.

Example 5

Analogously to Example 2, cyclo-(Arg-Gly-Asp(O-$(CH_2)_3$—CONH—$(CH_2)_3$-polymer)-Btd) (SEQ ID NO:11) is obtained by removal of the Mtr group starting from cyclo-(Arg(Mtr)-Gly-Asp(—O—$(CH_2)_3$—CONH—$(CH_2)_3$-polymer)-BTD) (SEQ ID NO:10).

Example 6

Analogously to Example 4, the following polymeric phase is obtained by condensation of polymer-O$(CH_2)_3$—$NH_2$ [commercially available] and cyclo-(Arg-Gly-Asp-Biph1): cyclo(Arg-Gly-Asp-(NH—$(CH_2)_3$-O-polymer)-Biph1).

The following is obtained analogously by condensation of cyclo-(Arg-Gly-Asp-Btd-Val) (SEQ ID NO:8) with $H_2N$$(CH_2)_3$—O—polymer: cyclo-(Arg-Gly-Asp(NH-$(CH_2)_3$—O—polymer)-Btd-Val)(SEQ ID NO:12).

The examples below relate to pharmaceutical preparations.

Example A: Injection vials

A solution of 100 g of a cyclopeptide of the formula I and 5 g of disodium hydrogenphosphate in 3 l of doubly distilled water is adjusted to pH 6.5 with 2 N hydrochloric acid, sterile filtered, filled into injection vials and lyophilized under sterile conditions, and the vials are sealed in a sterile manner. Each injection vial contains 5 mg of active compound.

Example B: Suppositories

A mixture of 20 g of active compound of the formula I is fused with 100 g of soya lecithin and 1400 g of cocoa butter, and the mixture is poured into molds and allowed to cool. Each suppository contains 20 mg of active compound.

Example C: Solution

A solution of 1 g of active compound of the formula I, 9.38 g of $NaH_2PO_4 \times 2H_2O$, 28.48 g of $Na_2HPO_4 \times 12H_2O$ and 0.1 g of benzalkonium chloride is prepared in 940 ml of doubly distilled water. The solution is adjusted to pH 6.8, made up to 1 l and sterilized by irradiation. This solution can be used in the form of eye drops.

Example D: Ointment 500 mg of active compound of the formula I are mixed with 99.5 g of petroleum jelly under aseptic conditions.

Example E: Tablets

A mixture of 100 g of a cyclopeptide of the formula I, 1 kg of lactose, 600 g of microcrystalline cellulose, 600 g of maize starch, 100 g of polyvinylpyrrolidone, 80 g of talc and 10 g of magnesium stearate is pressed to give tablets in a customary manner, such that each tablet contains 10 mg of active compound.

Example F: Coated tablets

Tablets are pressed as stated in Example E and then coated in a customary manner with a coating of sucrose, maize starch, talc, tragacanth and colorant.

Example G: Capsules

Hard gelatin capsules are filled with an active compound of the formula I in the customary manner, so that each capsule contains 5 mg of active compound.

Example M: Inhalation spray 14 g of active compound of the formula I are dissolved in 10 l of isotonic NaCl solution and the solution is filled into commercially available spray containers having a pump mechanism. The solution can be sprayed into the mouth or nose. One spray burst (about 0.1 ml) corresponds to a dose of about 0.14 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclopeptide compound according to formula I cyclo-(Arg-A-Asp-R$^1$-R$^2$)    I wherein A is Gly or Ala;

R$^1$ is a 2-carboxy-8-amino-4-thiapiperolidin-9-one (Btd) group; o-aminomethyl-o'-carboxybiphenyl (Biph) group; 2-aminomethyl-5-carboxymethyl-thiophene (Act) group; 2-(1,7-diazaspiro-[4,4]nonan-7-yl)-4-methylpentanoic acid ((S,S)spiro-Pro-Leu) group; or 2-(3-amino-1-pyrrolid-2-onyl)-4-methyl-pentanoic (S)Gly[ANC-2]-Leu or (R)Gly[ANC-2]-Leu) group; where the R$^1$ group is bonded by a peptide bond to the Asp and R$^2$ is absent, or else is Val, or a physiologically acceptable salt.

2. A cyclopeptide compound according to claim 1, (a) Cyclo-(Arg-Gly-Asp-(S)Gly[ANC-2]-Leu)(SEQ ID NO:5);

(b) cyclo-(Arg-Gly-Asp-(R)Gly[ANC-2]-Leu)(SEQ ID NO:6);

(c) cyclo-(Arg-Gly-Asp-(S,S)spiro-Pro-Leu)(SEQ ID NO:3);

(d) cyclo-(Arg-Gly-Asp-Act);

(e) cyclo-(Arg-Gly-Asp-Btd) SEQ ID NO:13);

(f) cyclo-(Arg-Gly-Asp-Btd-Val)(SEQ ID NO: 8); or (g) cyclo-(Arg-DAla-Asp-Btd-Val).

3. A pharmaceutical composition, comprising a cyclopeptide compound according to claim 2 and a pharmaceutically acceptable excipient.

4. A cyclopeptide compound according to claim 1, wherein the compound is a D- or L-enantiomer.

5. A pharmaceutical composition, comprising a cyclopeptide compound according to claim 4 and a pharmaceutically acceptable excipient.

6. A cyclopeptide compound according to claim 1, wherein R$^2$ is Val.

7. A pharmaceutical composition, comprising a cyclopeptide compound according to claim 1 and a pharmaceutically acceptable excipient.

8. A pharmaceutical composition according to claim 7, comprising 0.05–500 mg of the cyclopeptide.

9. A pharmaceutical composition according to claim 7, comprising about 0.5–100 mg of the cyclopeptide.

* * * * *